(12) United States Patent
Argentine

(10) Patent No.: US 8,876,877 B2
(45) Date of Patent: Nov. 4, 2014

(54) CENTERING FOR A TAA

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1094 days.

(21) Appl. No.: 12/428,636

(22) Filed: Apr. 23, 2009

(65) Prior Publication Data

US 2010/0274187 A1 Oct. 28, 2010

(51) Int. Cl.
| | |
|---|---|
| A61F 2/06 | (2013.01) |
| A61M 25/00 | (2006.01) |
| A61M 25/01 | (2006.01) |
| A61F 2/95 | (2013.01) |
| A61F 2/07 | (2013.01) |
| A61F 2/966 | (2013.01) |

(52) U.S. Cl.
CPC .............. *A61M 25/0082* (2013.01); *A61F 2/07* (2013.01); *A61M 25/0147* (2013.01); *A61M 2025/015* (2013.01); *A61F 2/95* (2013.01); *A61F 2002/9517* (2013.01); *A61F 2002/9665* (2013.01); *A61F 2002/9511* (2013.01)
USPC ....................................................... 623/1.11

(58) Field of Classification Search
USPC ........................ 623/1.11, 1.12, 1.13, 1.2, 1.23
See application file for complete search history.

(56) References Cited

U.S. PATENT DOCUMENTS

| | | | |
|---|---|---|---|
| 5,911,734 A * | 6/1999 | Tsugita et al. ................. | 606/200 |
| 6,033,378 A | 3/2000 | Lundquist et al. | |
| 6,676,692 B2 | 1/2004 | Rabkin et al. | |
| 7,264,632 B2 | 9/2007 | Wright et al. | |
| 2005/0049667 A1* | 3/2005 | Arbefeuille et al. ......... | 623/1.11 |
| 2007/0299499 A1* | 12/2007 | Hartley et al. ............... | 623/1.11 |
| 2008/0109059 A1 | 5/2008 | Gordon et al. | |
| 2008/0114390 A1* | 5/2008 | Guinan ......................... | 606/194 |
| 2008/0114440 A1* | 5/2008 | Hlavka et al. ................ | 623/1.12 |
| 2008/0114442 A1 | 5/2008 | Mitchell et al. | |
| 2008/0114443 A1 | 5/2008 | Mitchell et al. | |
| 2008/0208320 A1* | 8/2008 | Tan-Malecki et al. ....... | 623/1.17 |
| 2008/0215018 A1* | 9/2008 | Duffy et al. .................. | 604/284 |

FOREIGN PATENT DOCUMENTS

| | | |
|---|---|---|
| FR | 2779939 | 6/1998 |
| WO | WO96/09013 | 3/1996 |
| WO | WO2006/005082 | 1/2006 |
| WO | WO2008/034106 | 3/2008 |
| WO | WO2008/047092 | 4/2008 |
| WO | WO2008/112399 | 9/2008 |

* cited by examiner

Primary Examiner — Thomas McEvoy

(57) ABSTRACT

A stent graft is deployed by a steerable catheter delivery system having a integral tip capture release mechanism. The steering mechanism provides for a locked interference with a distal lock at the distal end of the delivery catheter. The configuration allows for selective circumferentially distributed release of one half or less of the number of crowns of a proximal spring which are captured by a tip capture mechanism so that new positioning of the stent graft can be verified and assured before full release of all proximal spring crowns is done. In this way, one or more steering elements of a catheter can be maintained in tension until catheter position is verified and acceptable stent graft position is achieved. This apparatus and method is particularly useful for deploying stent graft in curved passages such a thoracic aorta.

25 Claims, 21 Drawing Sheets

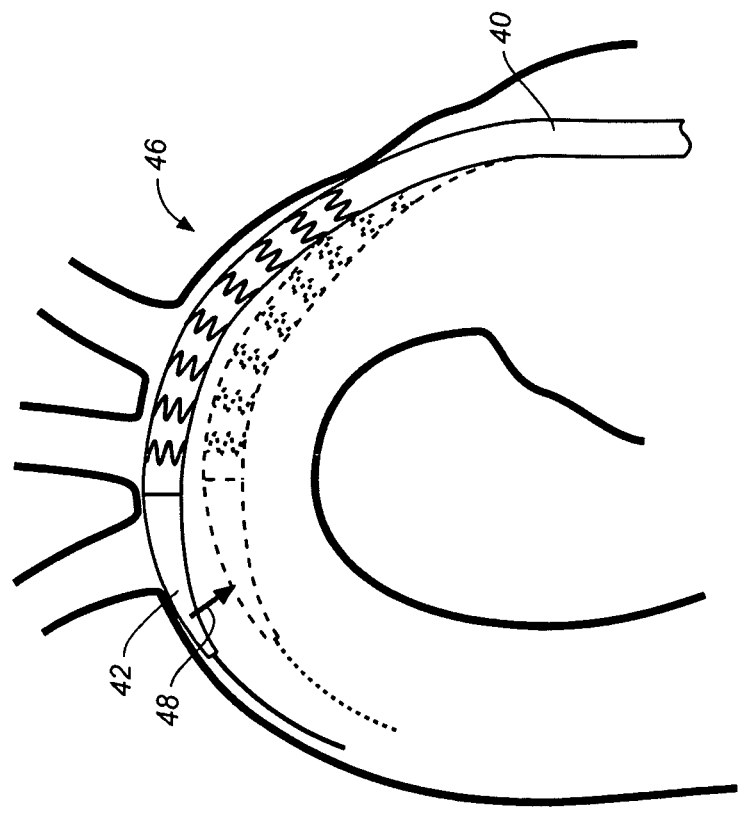
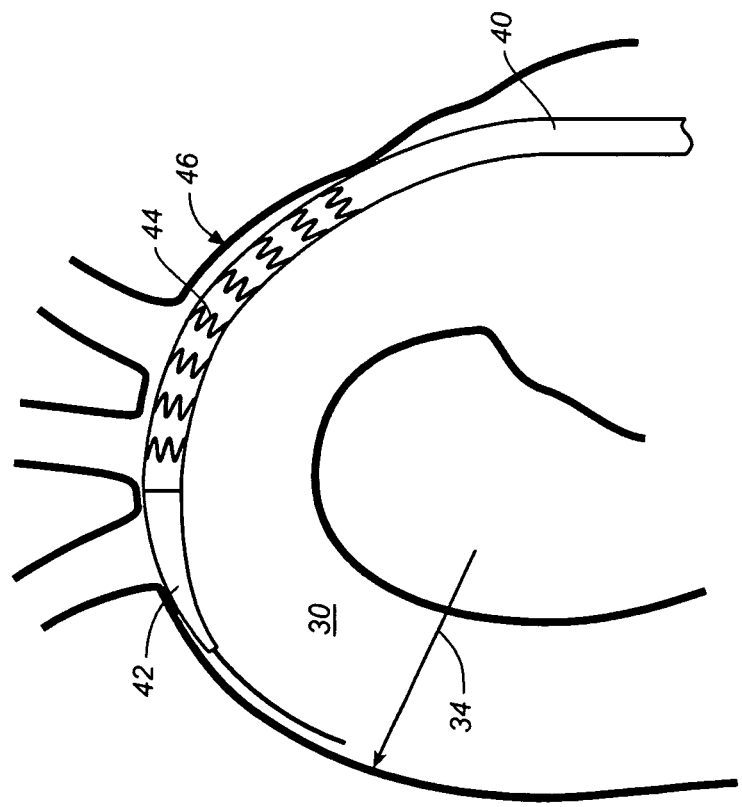
FIG. 2B
FIG. 2A

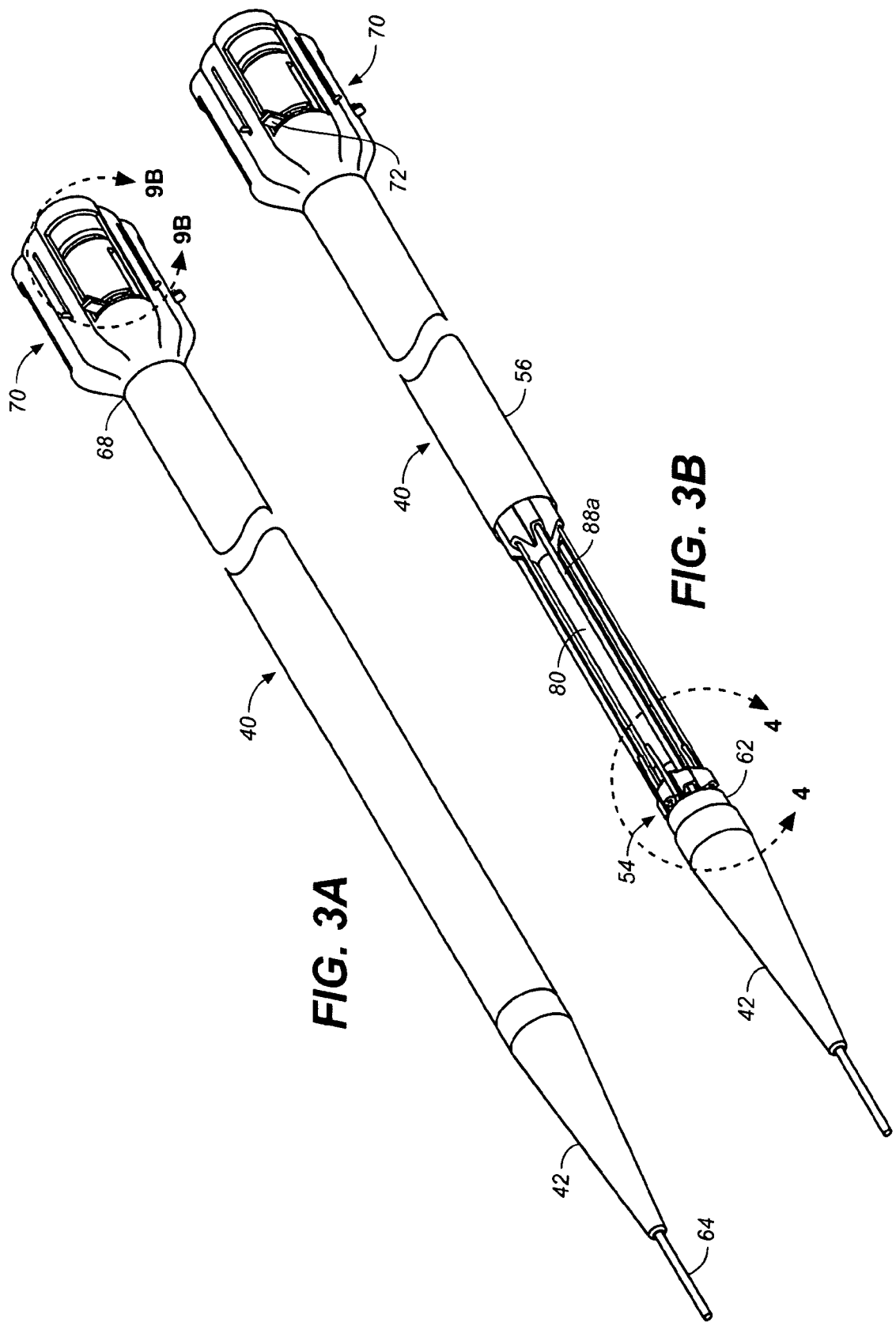

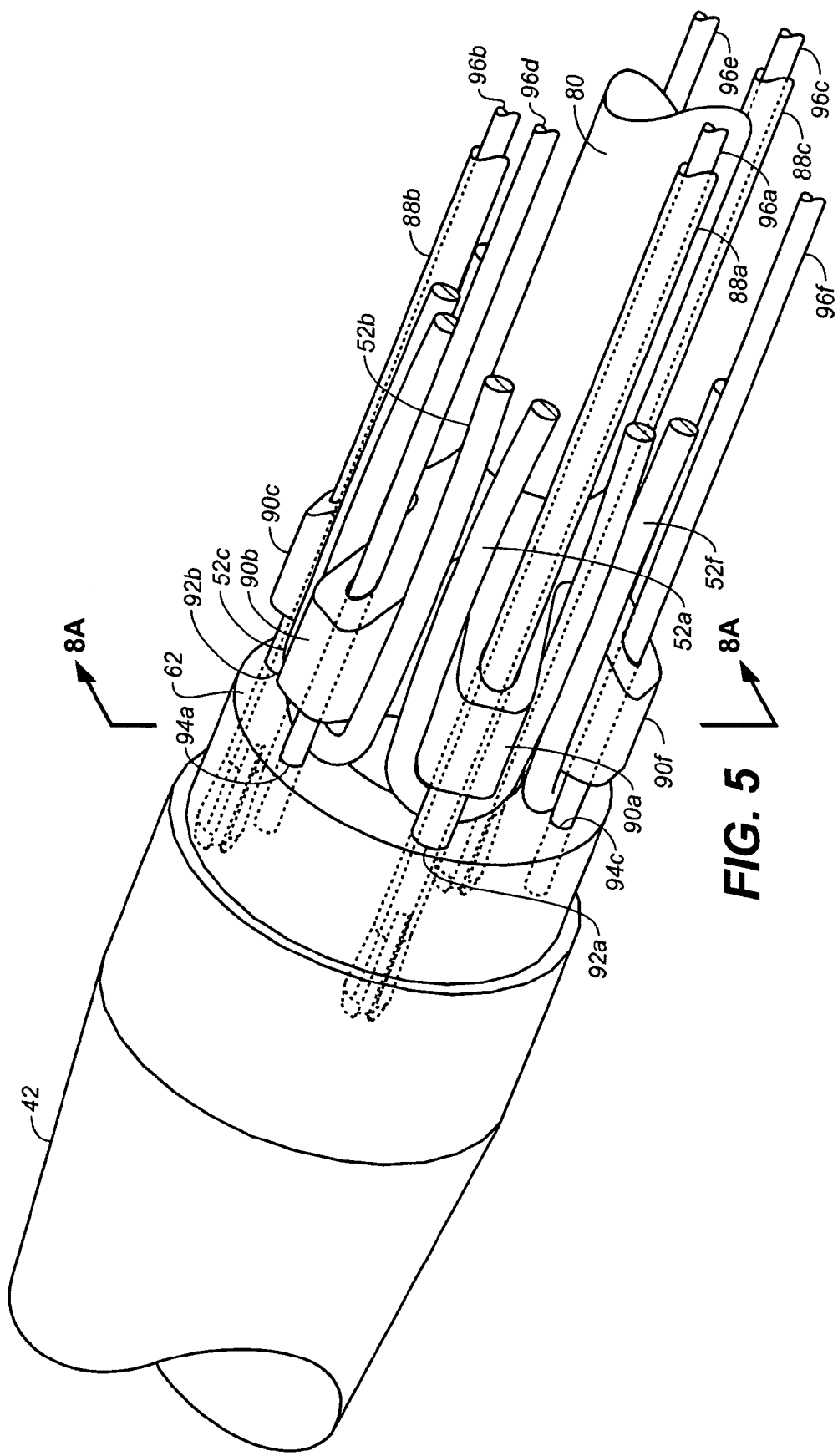

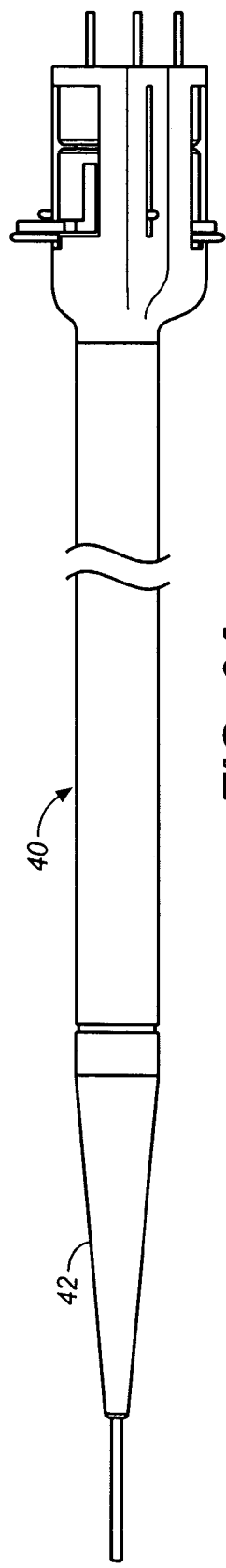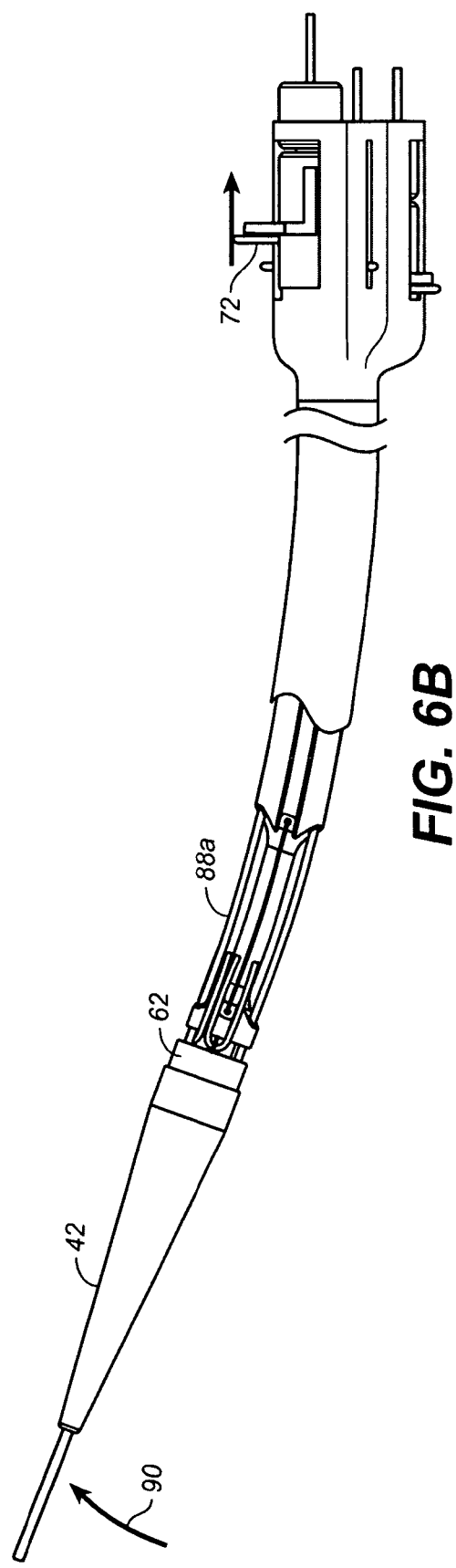

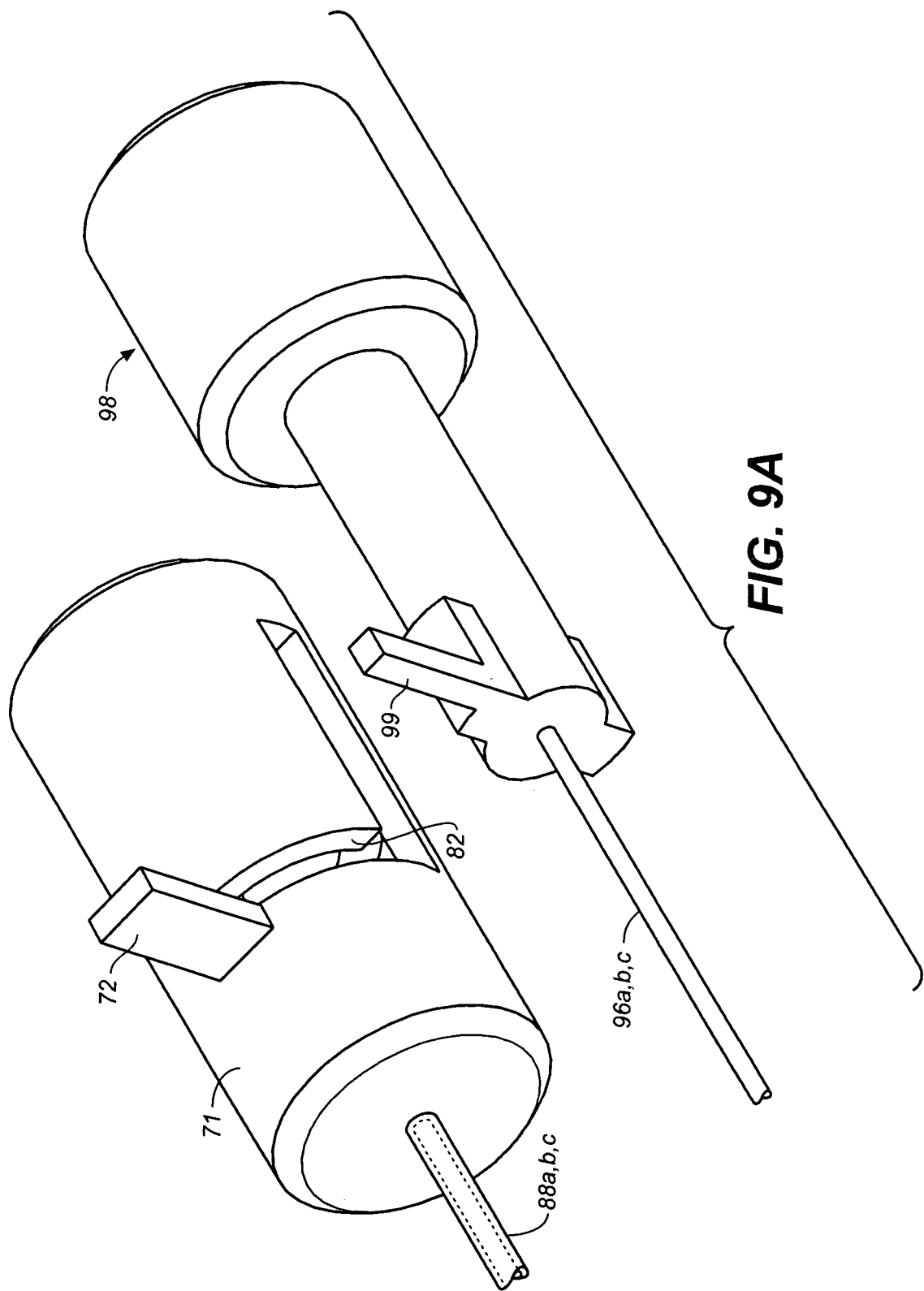

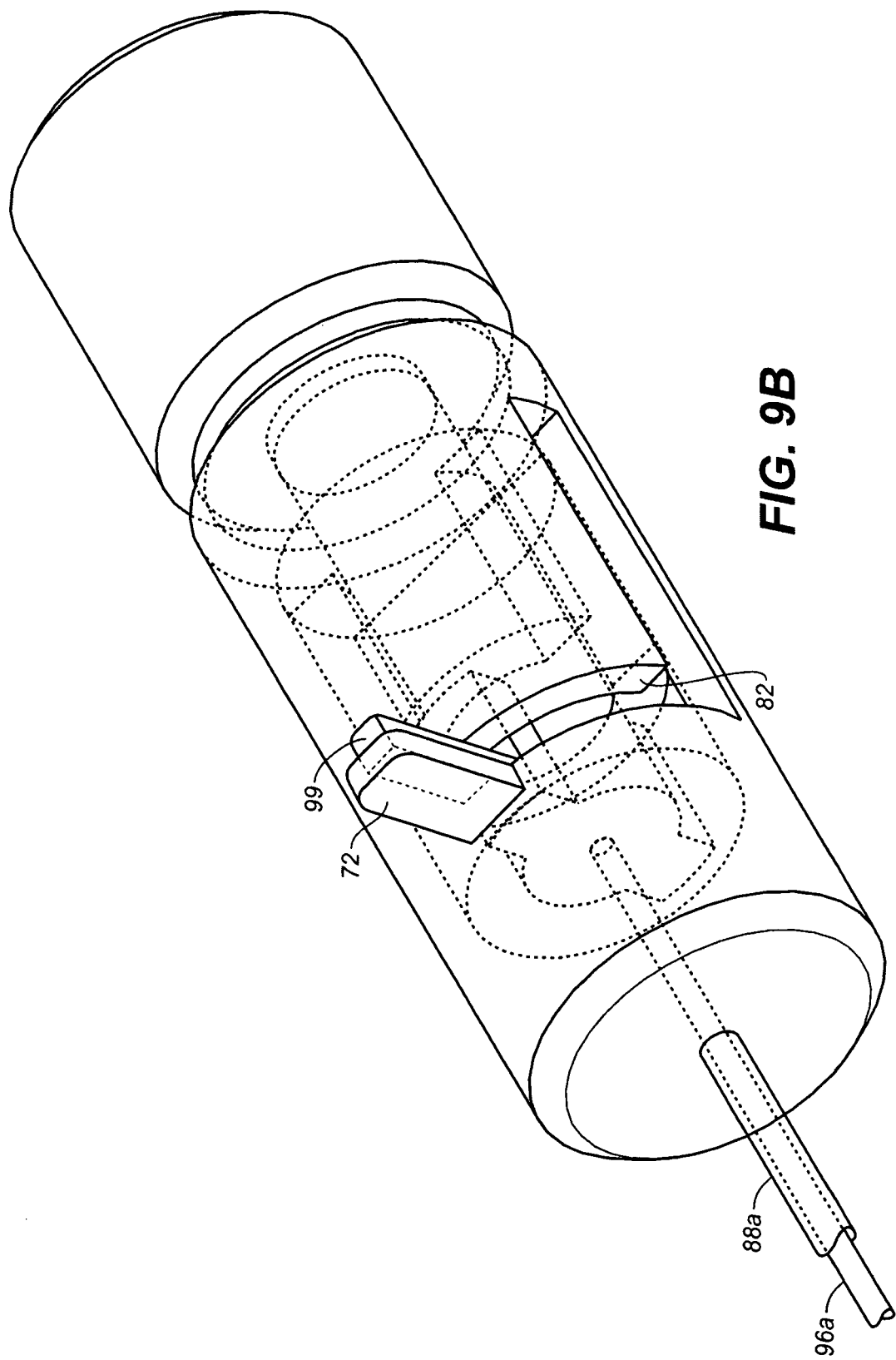

CENTERING FOR A TAA

FIELD OF THE INVENTION

This invention relates generally to a steerable tip capture TAA delivery system used to deliver stents and stent grafts.

BACKGROUND

This invention relates generally to medical devices and procedures, and more particularly to a method and system of deploying stent-grafts in a vascular system.

Prostheses for implantation in blood vessels or other similar organs of the living body are, in general, well known in the medical art. For example, prosthetic vascular grafts formed of biocompatible materials (e.g., Dacron® material or expanded, porous polytetrafluoroethylene (PTFE) tubing) have been employed to replace or bypass damaged or occluded natural blood vessels.

A graft material supported by a framework is known as a stent-graft or endoluminal graft. In general, the use of stent-grafts for treatment or isolation of vascular aneurysms and vessel walls which have been thinned or thickened by disease (endoluminal repair or exclusion) is well known.

Many stent-grafts, are "self-expanding", i.e., inserted into the vascular system in a compressed or contracted state, and permitted to expand upon removal of a restraint. Self-expanding stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent-graft implanted at a particular location is typically configured in a tubular shape with a diameter slightly greater than the diameter of the blood vessel in which the stent-graft is intended to be used. In general, stent-grafts are typically deployed through a minimally invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment in one example is effected using a delivery catheter with coaxial inner tube and sheath, arranged for relative axial movement. The stent-graft is compressed and disposed within the distal end of the sheath proximal to the distal end of the catheter and held by a stent stop or distal stent graft tip capture mechanism attached to a catheter shaft.

The catheter is then maneuvered, typically routed though a vessel until the end of the catheter (and the stent-graft contained therein) is positioned in the vicinity of the intended treatment site. The catheter shaft is then held stationary while the sheath of the delivery catheter is withdrawn. The catheter may include a stop or tip capture prevents the stent-graft from moving back as the sheath is withdrawn.

As the sheath is withdrawn, the stent-graft is gradually exposed (uncovered—released—deployed) from its proximal end. As the stent-graft is exposed it radially expands so that at least a portion of the exposed stent graft is in substantially conforming surface contact with a portion of the interior of the lumen, e.g., blood vessel wall.

In straight vessels, placement of the stent-graft is relatively straightforward. However, in complex vessels, e.g., in the aortic arch or other curved vessel, placement of the stent-graft is complicated by the tendency of the catheter to maintain a straight shape while the surround vessel curves.

More particularly, in the aortic arch, the stiffness of the delivery catheter causes the distal tip of the delivery catheter to position itself close to (if not conforming with) the vessel wall at the outer radius of curvature of the aortic arch. This offset positioning (to the outer radius) of the distal tip of the delivery system combined with the effect blood flow forces have on the stent-graft as it is deployed, results in a high likelihood that the stent graft will be deployed asymmetrically.

FIG. 1A shows a stent graft deliver catheter 20 containing a stent graft 22 substantially conforming to the outside radius of curvature of the thoracic aorta 30. As shown in FIG. 1B when the stent graft begins to deploy, the blood flow, shown by the arrow 32, causes the initial deployment of the bare spring 24 at the proximal end of the stent graft 22 to open unevenly such that the portion of the spring closer to the inner radius of the thoracic arch bends outward (from the centerline of the stent graft) and downward. As a result, the proximal end 26 of the stent graft 22 is not orthogonal to the vessel wall (see FIG. 1C).

To reiterate, as stent-graft 22 deployment begins, the blood flow (e.g., 32) catches the initially deployed springs (e.g., 24) like a sail of a sail boat and causes some springs and or stent graft portions to bend preferentially in the direction of blood flow. This causes uneven deployment such that the portion of the springs or stent graft closer to the inner radius of curvature of the aortic arch bends out (inward with respect to the radius of curvature as shown in FIGS. 1B and 1C) from the stent graft and downward when deployed high in the vessel as shown. As a result, the proximal end of the stent-graft is not deployed orthogonal to the wall of the aortic arch. To correct the initial asymmetrical deployment, the physician typically tries to reposition the stent-graft, which is generally undesirable (as vessel wall abrasion and more extensive injury may result) depending upon the particular stent graft and anatomical geometry involved. Further, due to the repositioning, additional cuff (extender) type stent-grafts may need to be deployed.

As described herein: the proximal end of the stent-graft is the end closest to the heart by way of blood flow path whereas the distal end is the end furthest away from the heart as deployed. In contrast and of note, the distal end of the delivery catheter is usually identified to the end that is farthest from the operator (handle) while the proximal end of the catheter is the end nearest the operator (handle). For purposes of clarity of discussion, as used herein, the distal end of the delivery catheter is the end that is farthest from the operator (the end furthest from the handle) while the distal end of the stent-graft is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system proximal and distal designations may be consistent or opposite in actual usage. When using femoral artery access the distal ends are opposite in the device and catheter, while when using a brachial artery access they are consistent.

SUMMARY OF THE INVENTION

A device and method of deploying a stent-graft in a curved vessel using features of a steerable catheter and a tip release mechanism in one delivery catheter system are provided. The steering mechanism centers the distal tip of the delivery system and thereby a proximal end of the stent-graft in the curved vessel. A sheath of the stent-graft delivery system is retracted to expose the proximal end of the proximal spring of the stent-graft captured in the catheter tip capture mechanism. The stent-graft is held centered in the vessel and a fractional (less than all) portion of the crowns held by the tip capture mechanism are initially released to partially stabilize the stent graft in the curved vessel as it self expands to deploy. After further deployment of the stent-graft, the tension on the delivery system tip steering mechanism is relaxed and crowns of the proximal end of the stent-graft still captured in the delivery system tip capture mechanism are released.

By steering the delivery catheter to center the end of the catheter containing the stent-graft prior to deployment and simultaneously using tip capture to prevent uncontrolled outward bending of the proximal spring of the stent graft, the initial deployment of the stent-graft (the proximal edge of it stent graft material) is substantially orthogonal to the axial centerline of the curved vessel at the deployment location. As the initial deployment of the stent-graft is symmetric, the need to reposition the stent-graft after initial deployment may be avoided. Accordingly, the initially deployed stent-graft is accurately placed within the curved vessel and the need to deploy additional stent-grafts is eliminated.

These and other features will be more readily apparent from the detailed description set forth below taken in conjunction with the accompanying drawings.

BRIEF DESCRIPTION OF DRAWINGS

FIGS. 2A-E show schematic cross sectional illustrations of a delivery system having a steerable element with a tip capture elements to steer the delivery catheter in the vessel and provide tip capture capabilities during deployment.

FIG. 3A shows a schematicized perspective view of a delivery catheter as shown in FIG. 2A.

FIG. 3B shows a cut away view of FIG. 3A with part of the sheath removed and no stent graft shown in position within the sheath.

FIG. 5 shows a close up view of the distal portion of the delivery catheter 40 shown in FIG. 4, viewed from a handle end of the catheter.

FIGS. 6A and 6B provide a side schematicized view of the catheter of FIG. 2A in a straight and bent configurations and its operation with respect to its handle.

FIGS. 9A-B, 10A-B, 11A-C, and 12A-C show schematicized perspective, side, and end views of the elements and progressive steps of deployment as performed and observed for a particular steering member and release member control elements at the handle of the delivery catheter deploying a stent graft as shown in FIGS. 2A-E.

DETAILED DESCRIPTION

Figure 1B:
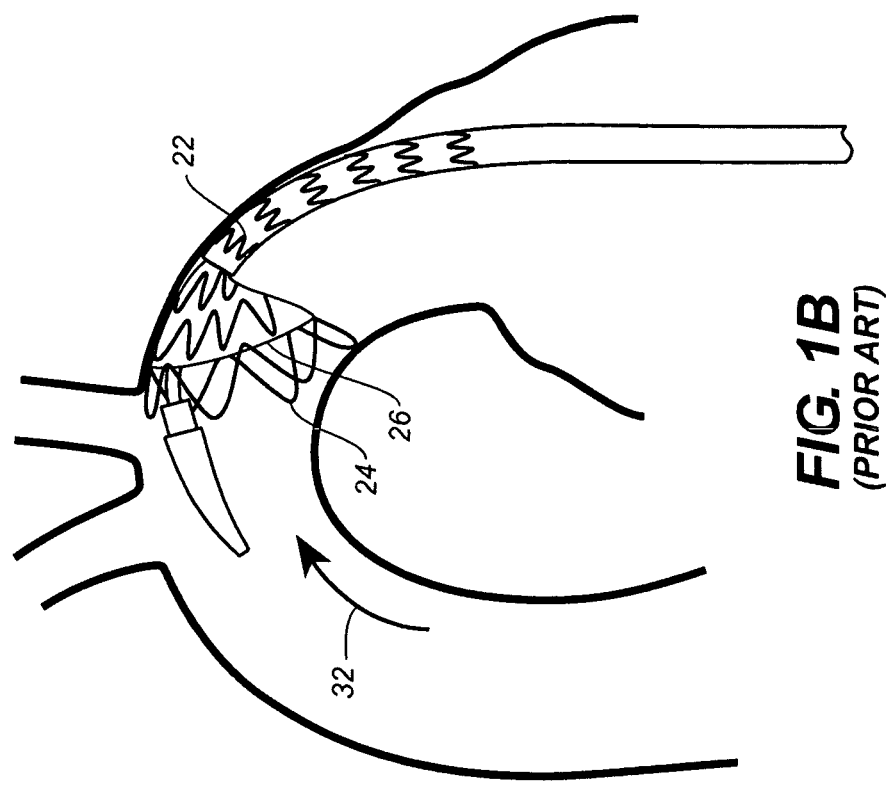
FIGS. 1A-C show progressive schematic cross sectional views of a prior art delivery system deploying a stent graft asymmetrically.
Figure 1A:
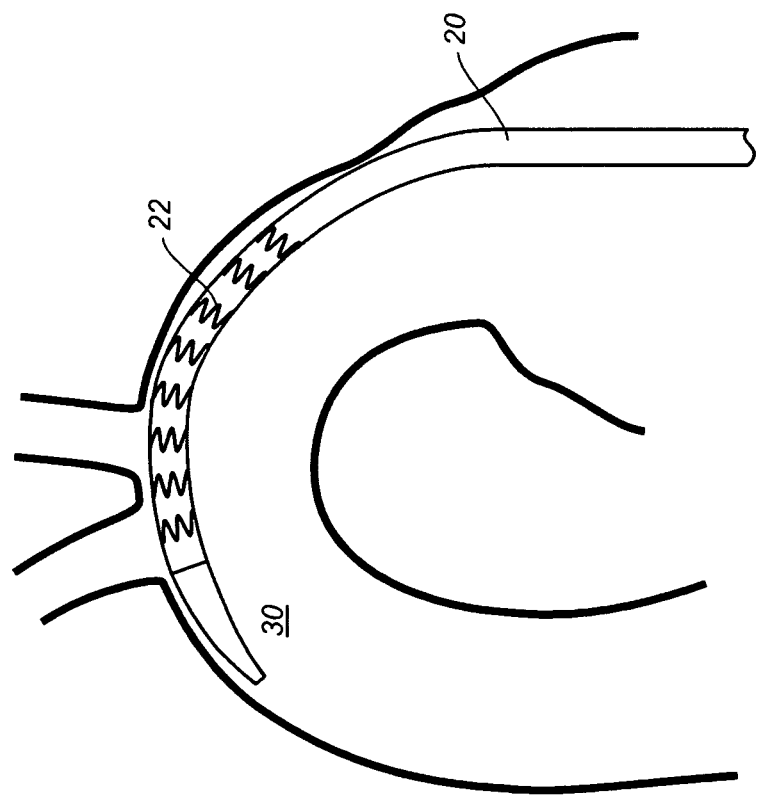
Figure 1C:
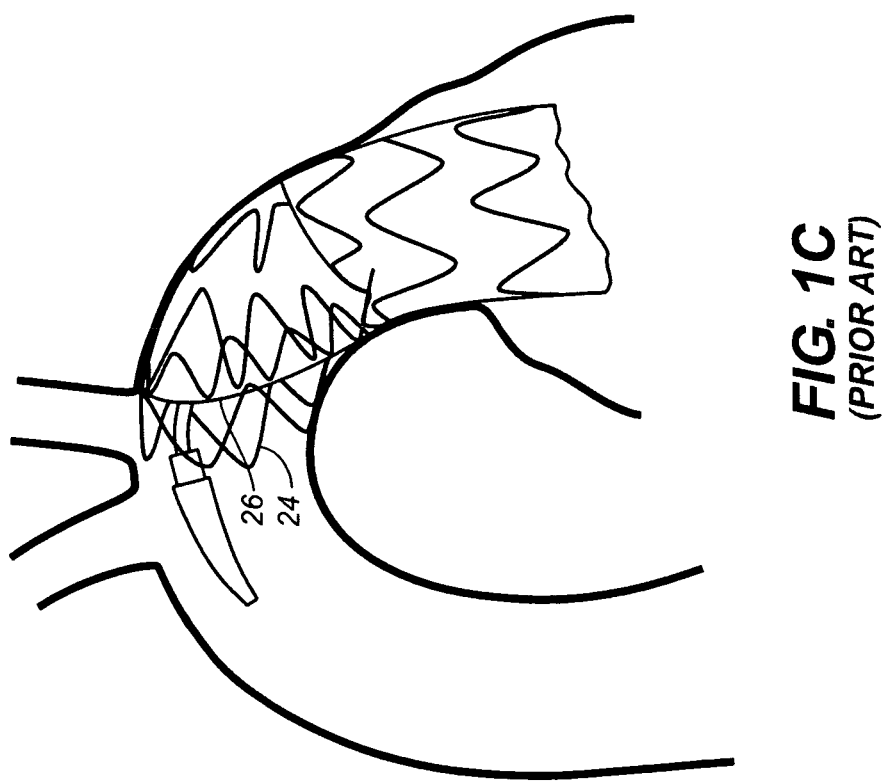
Figure 2C:
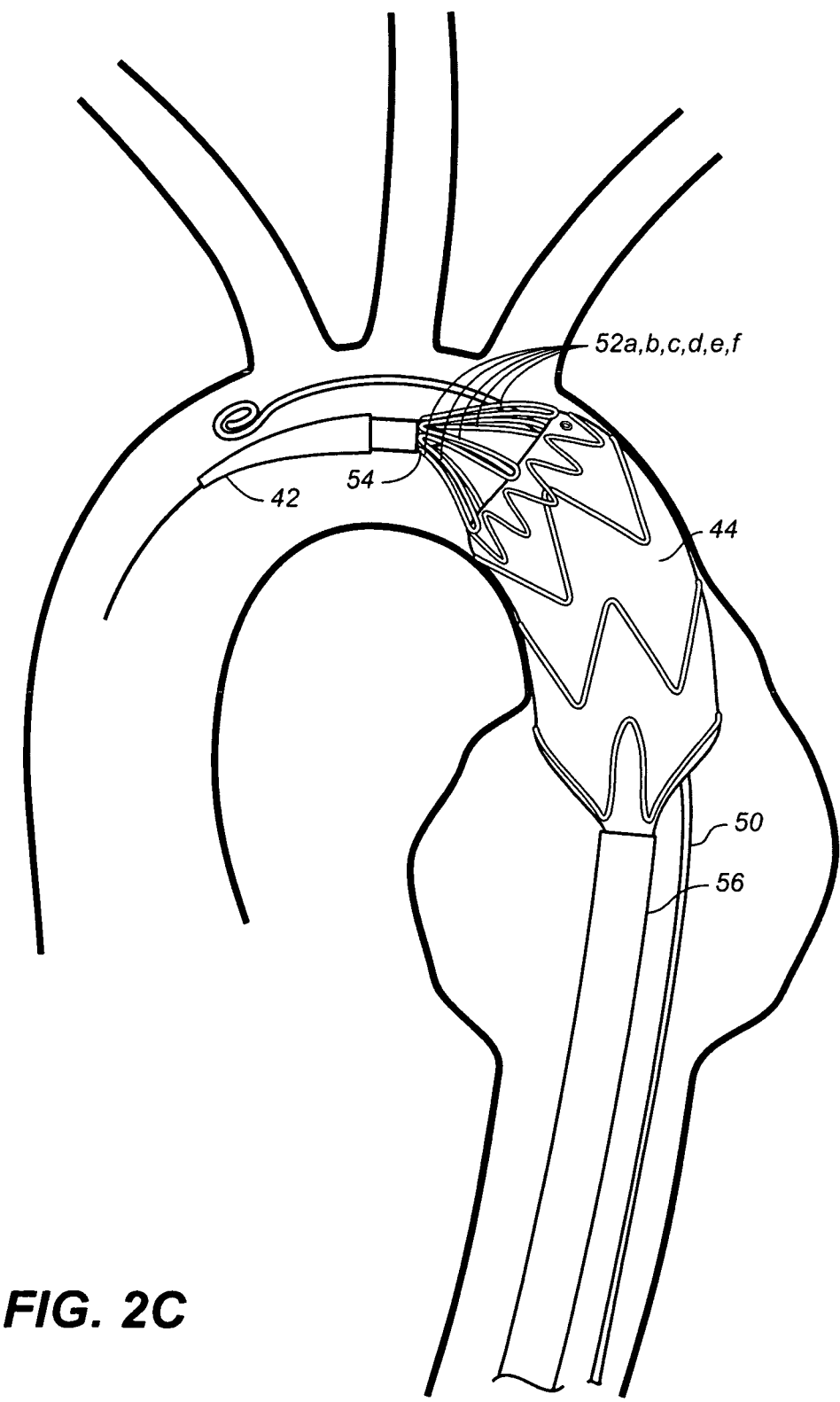
Figure 2D:
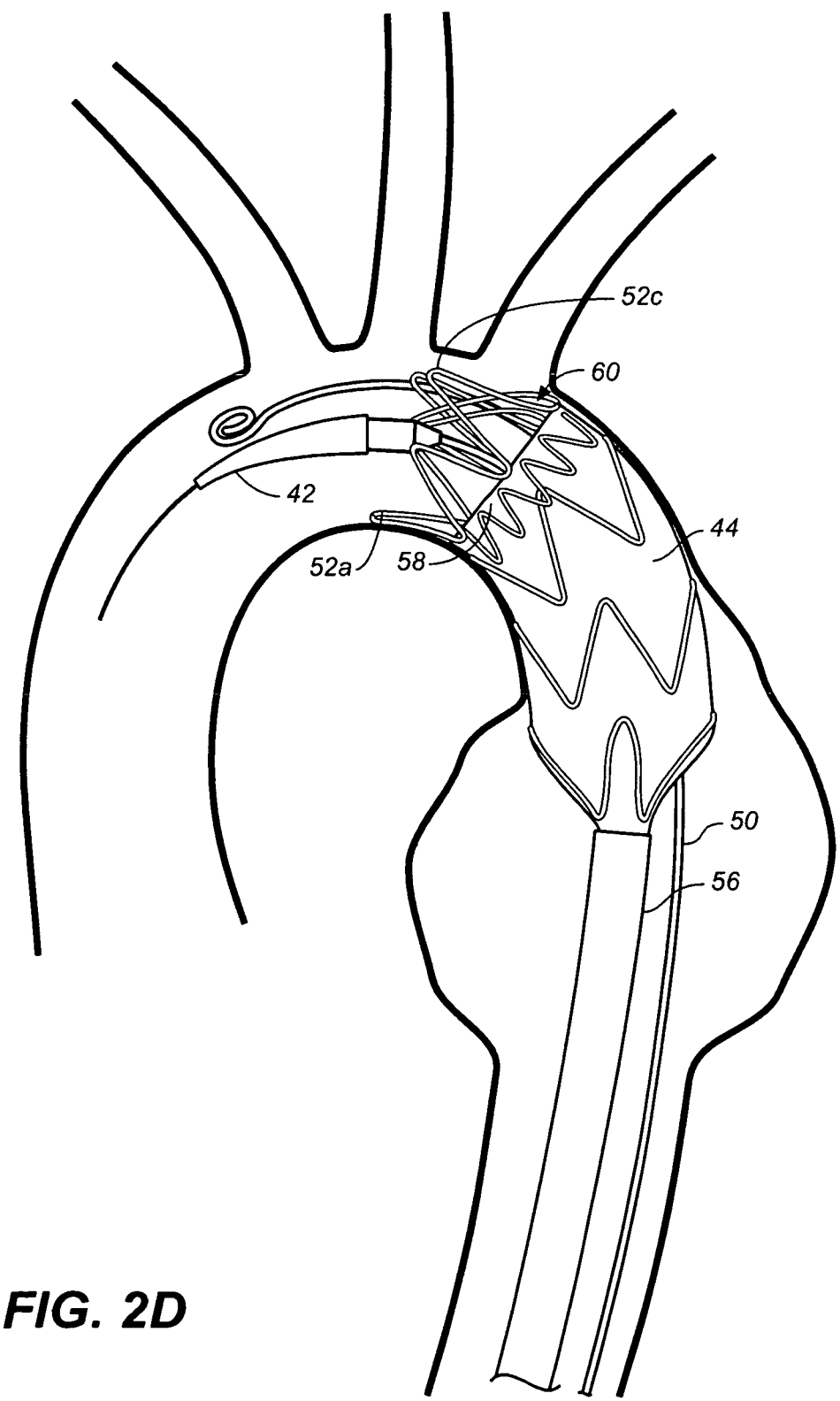
Figure 2E:
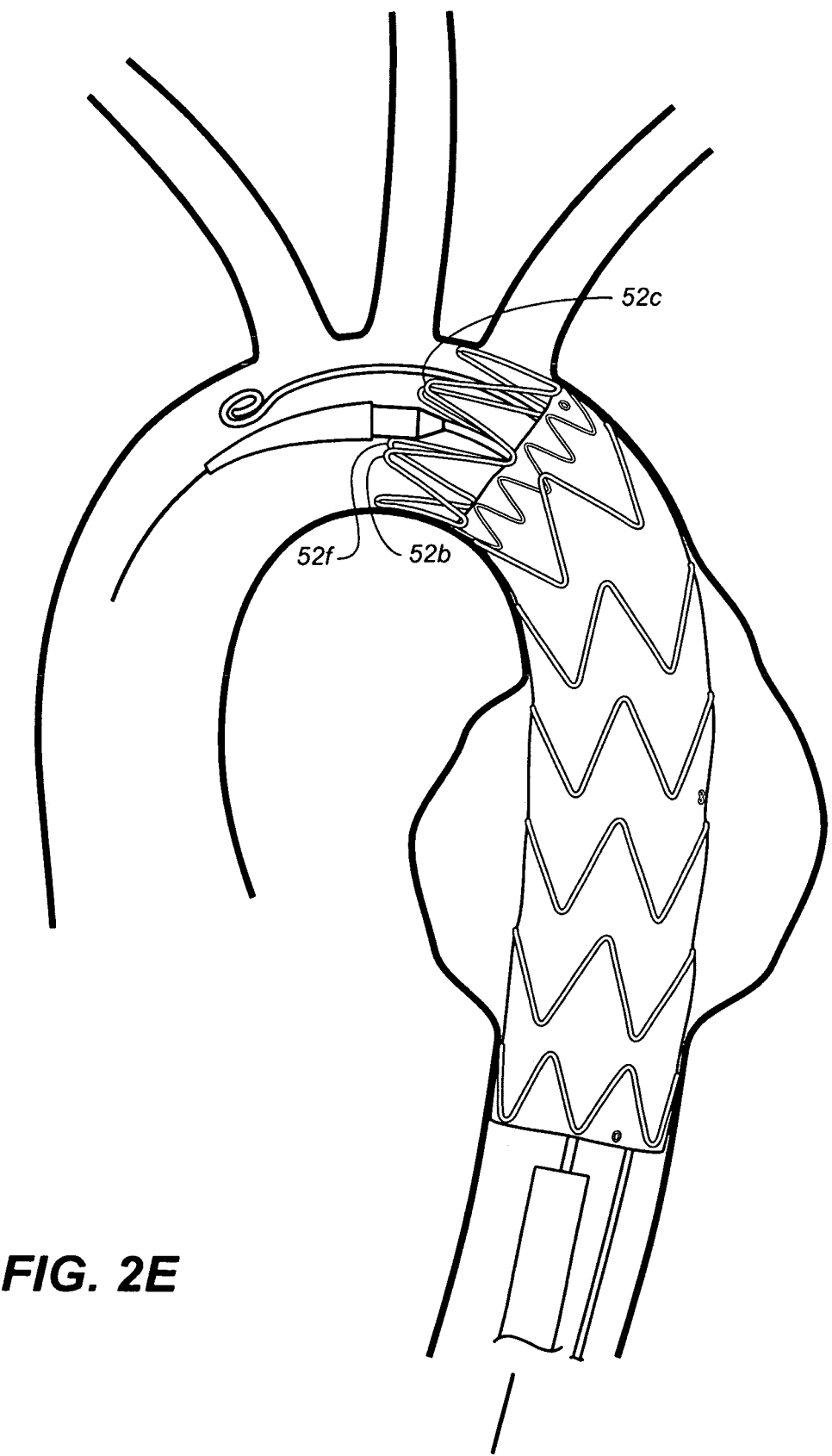

A steerable catheter with a integral tip release mechanism is described below. An aortic arch 30 containing a delivery catheter 40 (having a tip 42 and containing a stent graft 44) conforming to the outside radius of curvature 34 of the arch 33, is shown in FIG. 2A. Since the tip 42 of the deliver catheter 40 naturally lays along the outer radius of the arch away from the center of the vessel, a steering mechanism (later described) is used to move the tip of the tip 42 of the catheter and it's distal end 46 towards the center of the vessel (as shown by the moving arrow 48 showing the distal end 46 of the delivery catheter 40 being moved to the center of the vessel in FIG. 2B). Once moved to the center of the vessel and held there as shown in the dashed-line representation as shown in FIG. 2B, the sheath of the delivery system can be retracted to begin deployment of the stent graft 44. A contrast injection catheter 50 may be used to position the longitudinal position of the delivery catheter 40 with respect to branching arteries, e.g., 28. When the sheath 56 is partially retracted the stent graft can be, if needed, manipulated to be positioned (longitudinally and radially) as desired. Initially as shown in FIG. 2C all of the crowns 52a,b,c,d,e,f, are captured in the tip capture mechanism 54 of the tip 42. Once the physician is confident that the proximal end 58, i.e., proximal edge of the graft material, of the stent graft 44 is positioned correctly (in proximity to, but not obstructing) with respect to the branch arteries and is substantially orthogonal to the center line of the blood vessel partial deployment (release) of half of the six crowns of the proximal spring 60, i.e., 52a, 52c, and 52e, as shown in the FIG. 2D provide initial stabilizing and centering forces to radially center the proximal end 58 of the stent graft 44 and the still connected distal end of the delivery catheter in the vessel. The sheath 56 is then further retracted to fully deploy the stent graft and the remaining undeployed crowns 52b, 52d, and 52f are released from the tip, thereby fully releasing the stent graft 44 into the thoracic aorta 30, as shown in FIG. 2E.

The delivery mechanism performing the above described delivery of the stent graft is pictured in FIG. 3A. The delivery catheter 40 has a tip 42 which is shown being delivered over a guidewire 64. A handle 70 at the proximal end 68 of the delivery system provides a mechanism to steer and release the stent graft from the catheter as earlier described.

FIG. 3B shows a partial cut away view of the delivery catheter 40 with the stent graft not shown, except for a short wire representing a crown of a stent graft as it might be situated in the tip capture mechanism 54 of the delivery system 40. A catheter shaft 80 extends from the handle 70 to the catheter tip 42 and provides a guidewire lumen therein. The catheter shaft in this configuration is made from a splined shaft which has been centerless ground to remove the splines in the area where the stent graft is held. The center shaft 80 is made of PEEK. At least one steering member 88a extends from the handle 70 to a distal anchor 62, which in this embodiment is part of the tip 42. The steering member 88a can be pulled by steering tabs (e.g., 72) in the handle such that tension applied to the steering tab 72 causes tension in the steering member 88a to shorten the length of the catheter on the side of the steering member, causing the catheter to bend in that direction.

Such bending is illustrated in the comparisons of the side view of the delivery catheter shown in FIGS. 6A and 6B where steering tab 72 is retracted causing the steering member 88a to create tension on the side of the catheter pulling the distal anchor 62 preferentially towards the handle on the side of tension causing a bending or deflection as shown by the arrow 90 in FIG. 6B.

Figure 4:
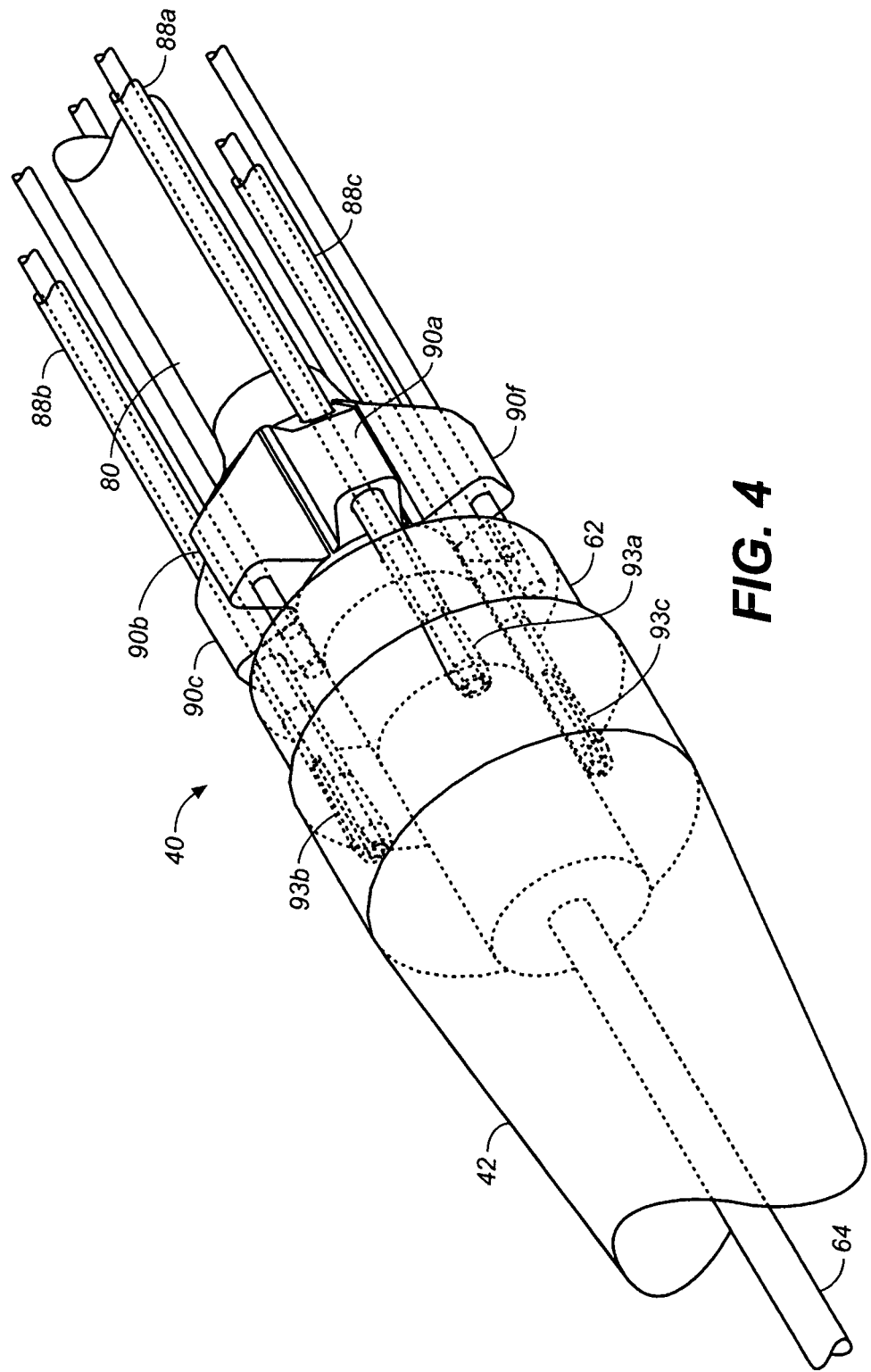
FIG. 4 shows a close up view of the distal end of the delivery catheter 40 shown in FIG. 3B, viewed from a tip end of the catheter.

FIGS. 4 and 5 show close up views of the tip and distal anchor of the delivery catheter 40. The catheter shaft 80 having been centerless ground to accommodate the bulk of the stent graft in the space below splines 90a,b,c,d,e,f. The splines as shown here have through holes to accommodate steering members 88a, 88b, 88c which are hollowed tubes made of a polymer material such as PEEK tubing. The steering members 88a,b,c, extend into steering member receiving openings 92a,b,c in distal anchor 62, which in this embodiment is part of the tip 42. Release members 96d,e,f extend through alternate splines, i.e., 90b, 90d, 90f, to provide, in this embodiment, capture and release capabilities for alternate crowns of a proximal spring of a stent graft.

In FIG. 5, crown portions, 52a,b,c,d,e,f, are shown captured in the space between the top of the splines, i.e., 90a,b, c,d,e,f, and the bottom of the distal anchor 62. The surface of the distal anchor 62 facing the splines, e.g., 52a have three steering member receiving openings 92a,b,c, and three release member receiving openings 94a,b,c therein. The steering member receiving openings, e.g., 92a,b,c, each lead to an expanding diameter conical hole (e.g., 93a,b,c) which is an enlarged diameter cavity inside the distal anchor 62 so that a distal end of the steering members 88a,b,c, can be placed there in an expanded to be locked in place by release members 96a, 96b, 96c, to act as a core element to create a mechanically interfering engagement to prevent the removal of an expandable locking elements such as a expanding collet as pictured in FIG. 5 and as further described below.

Figure 7A:
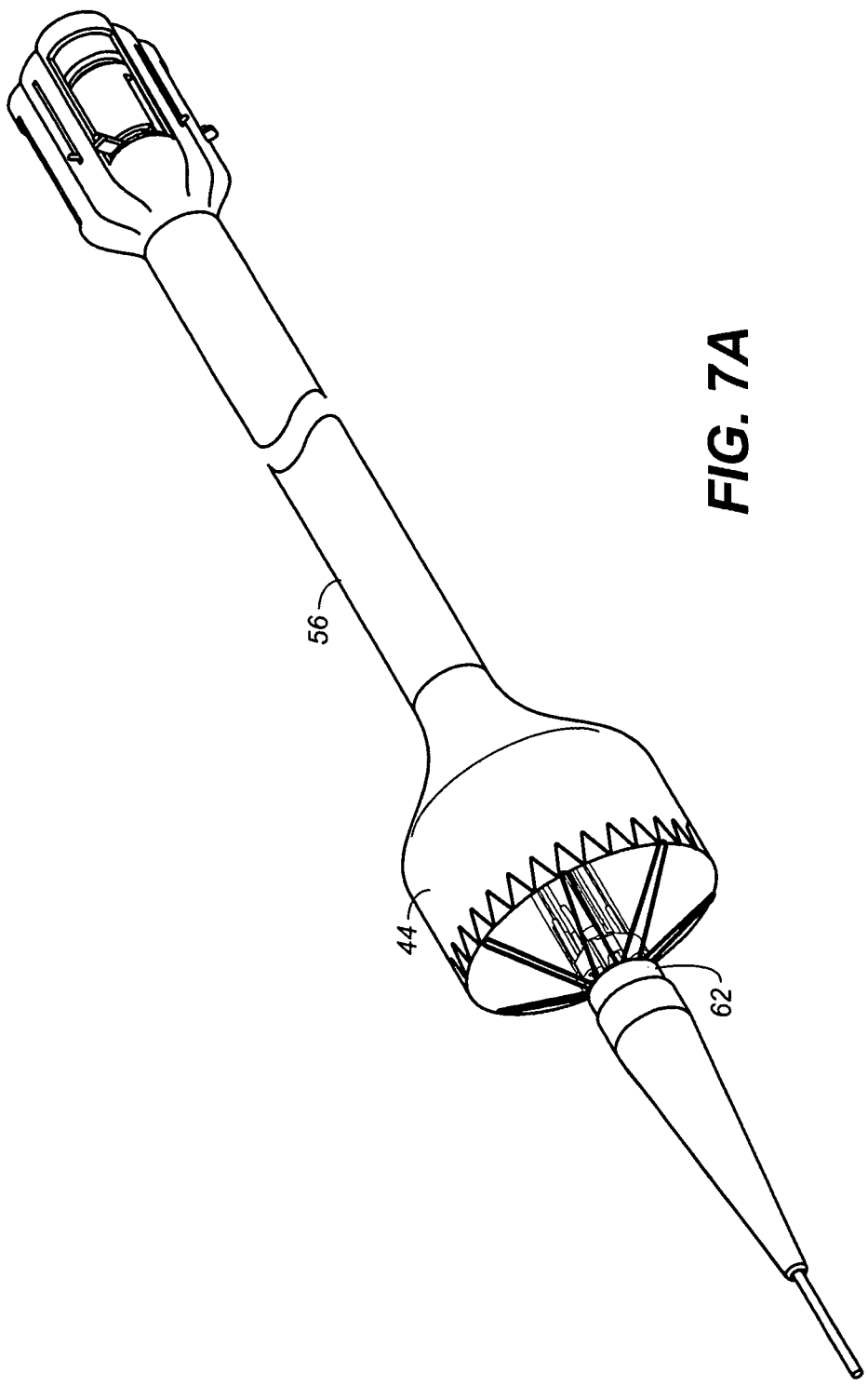
FIGS. 7A-C provide schematicized perspective views of the progressive steps of deployment of a stent from the delivery catheter as shown in FIG. 2A-E.
Figure 7B:
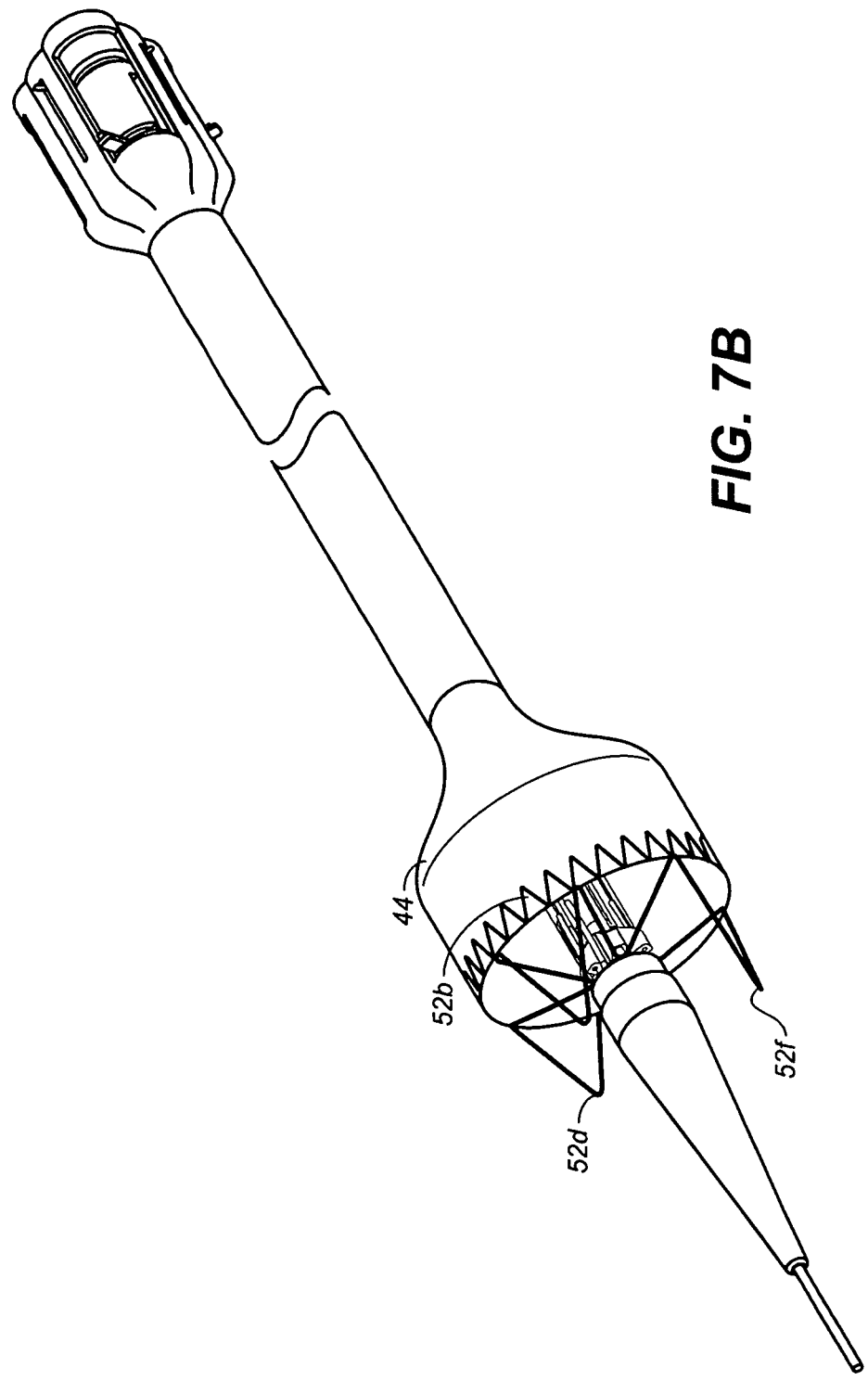
Figure 7C:
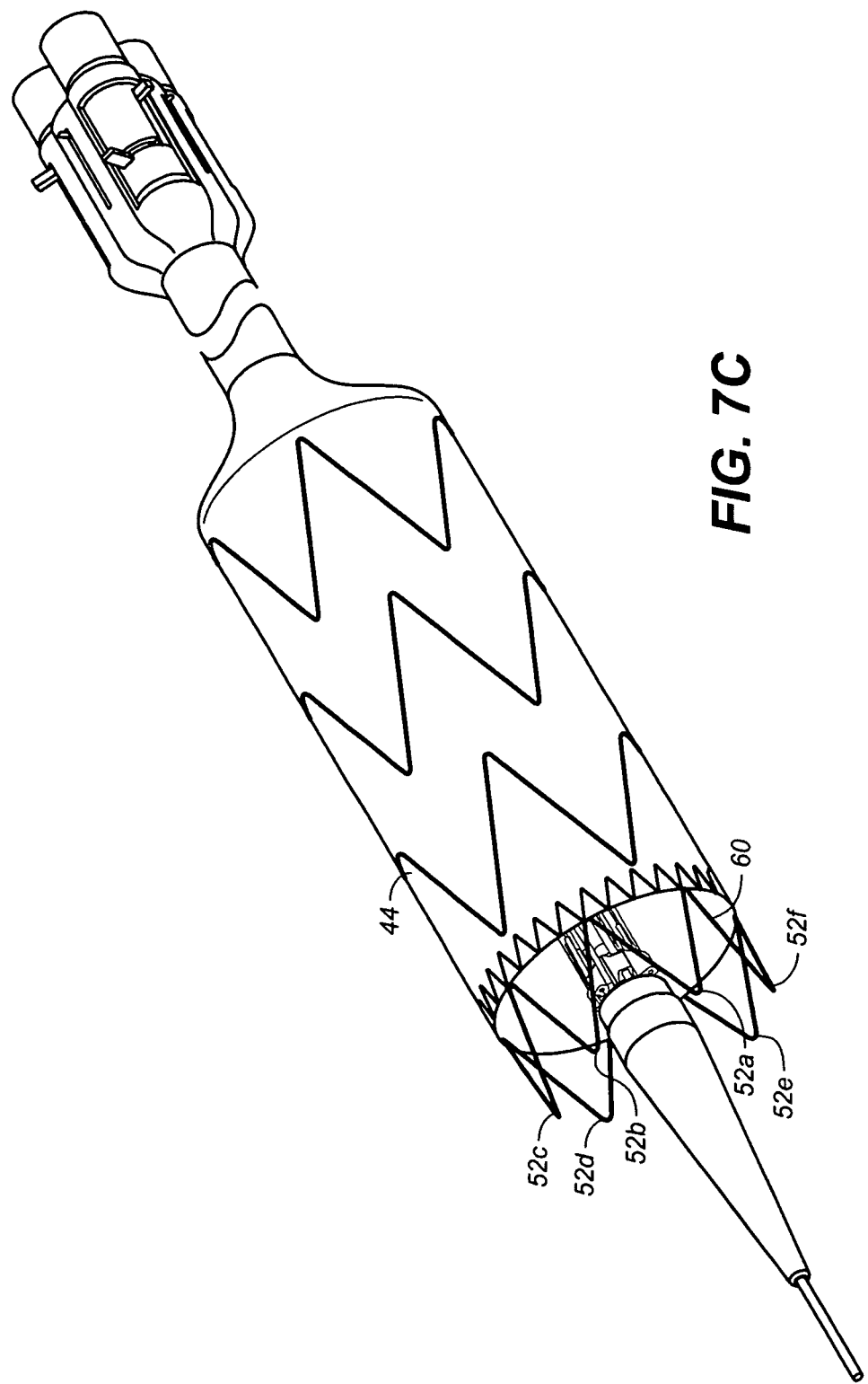
Figure 8A:
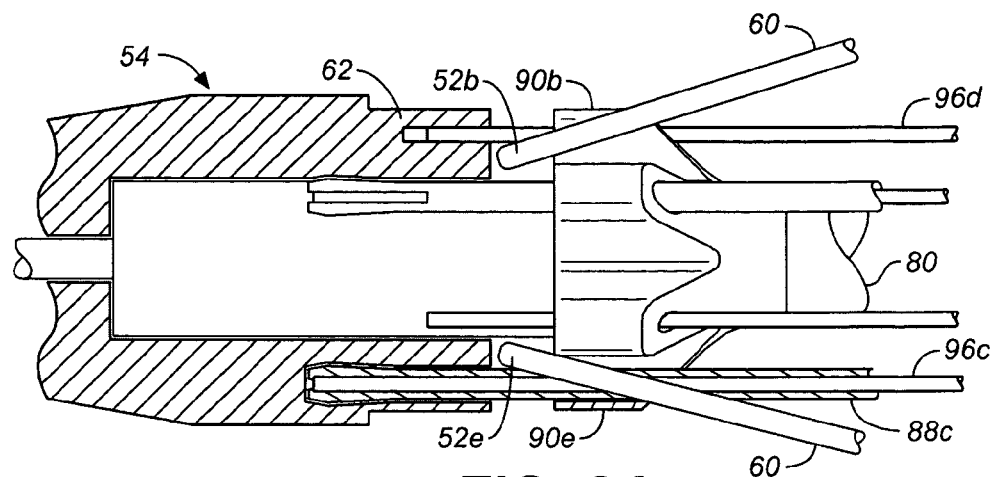
FIGS. 8A-D shows schematicized cross section of the progressive steps and motions associated with deployment of the stent graft from the delivery system as shown in FIGS. 2A-E.

The progressive and partial release of crown elements of the proximal stent spring 60 of a stent graft to be deployed will be described with reference to FIGS. 7A-C, 8A-D. A partially deployed stent graft and it's tip in captured condition is shown in FIGS. 7A and 8A. The sheath 56 having been partially retracted using mechanisms known to persons of ordinarily skilled in the art (therefore will not be described herein). The crowns 52a,b,c,d,e,f, of the proximal spring 60 are shown captured within the space between the splines, e.g., 90a,b and the distal anchor 62. Meanwhile though the sheath 56 has been partially retracted none of the crowns are free to move from the tip capture mechanism 54. As can be seen in the schematicized cross-section of FIG. 8A, the crown 52b is captured in the space between the catheter shaft 80 and the distal anchor 62, the spline 90b, and a distal portion of release member 96d. The stent crown 52e is similarly captured between spline 90e, distal anchor 62, catheter shaft 80, and steering member 88c which is reinforced and locked in place by release member 96c passing along a center line thereof to a distal end of the steering member 88c.

Figure 8B:
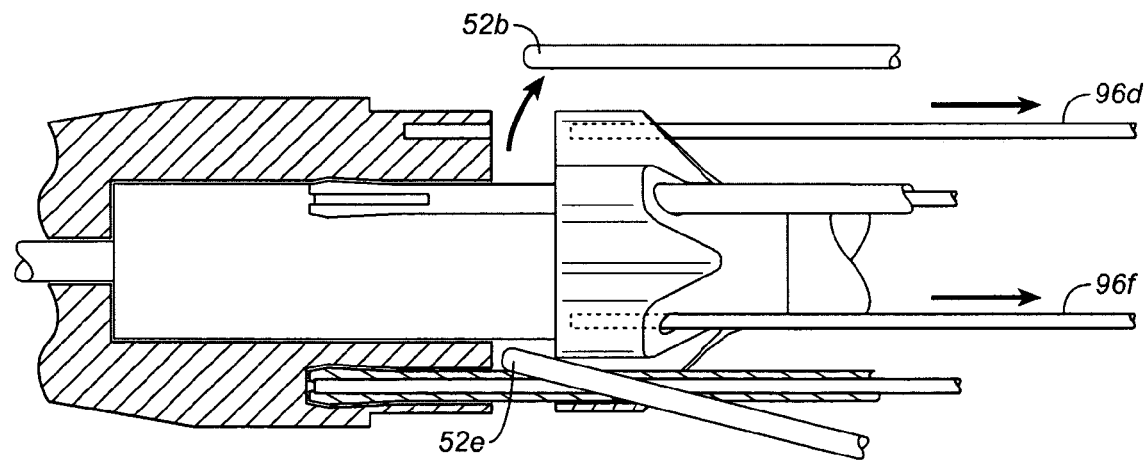
Figure 8C:
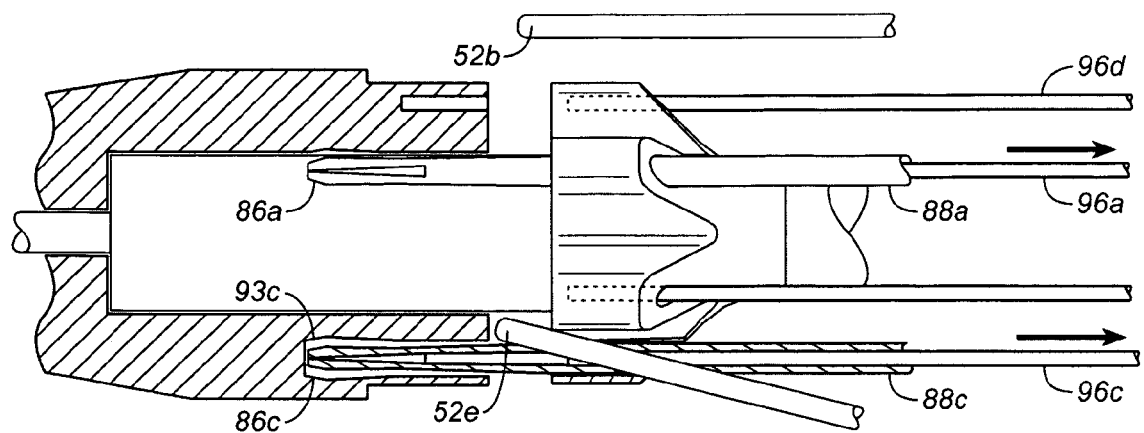
Figure 8D:
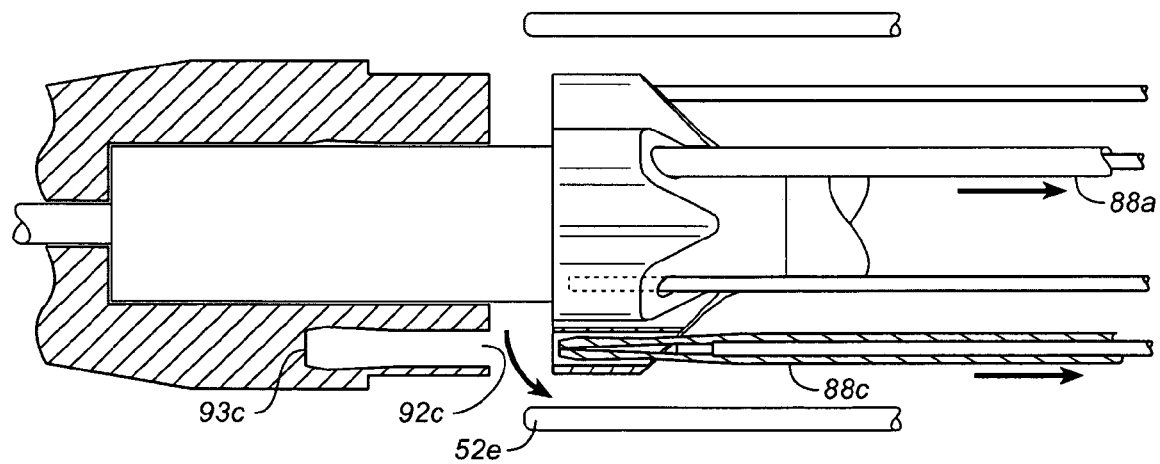
Figure 10A:
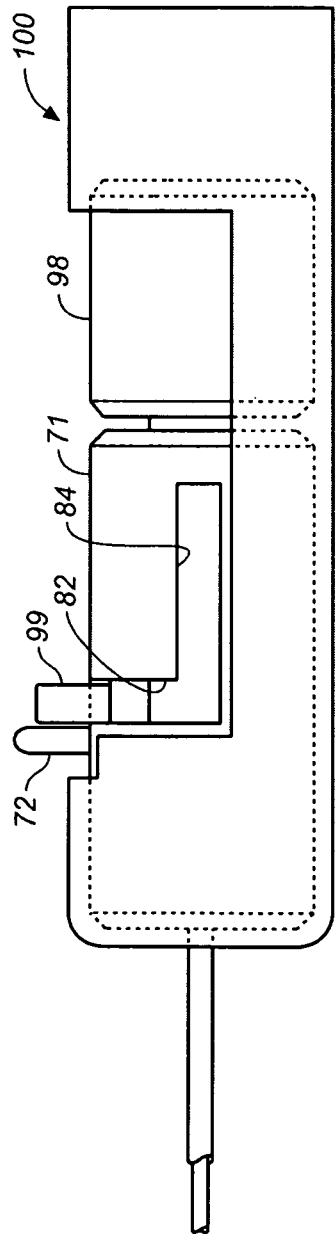
Figure 10B:
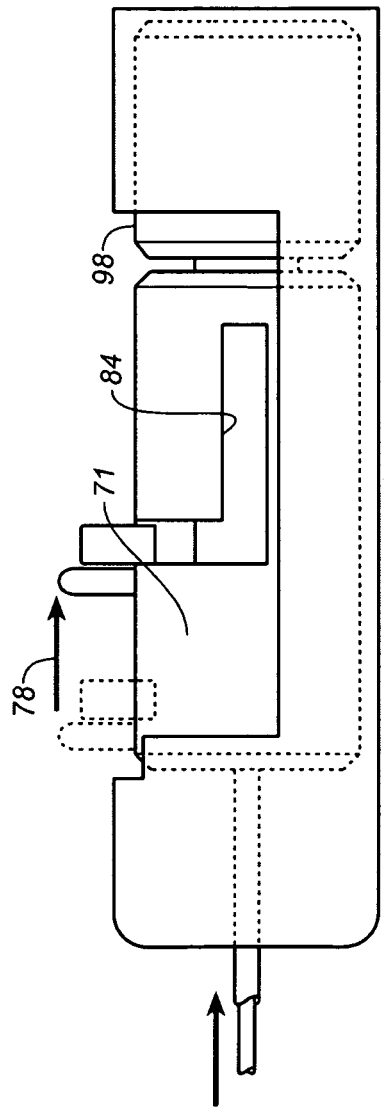
Figure 12A:
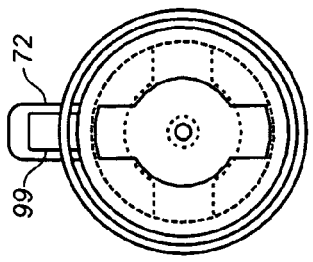
Figure 12B:
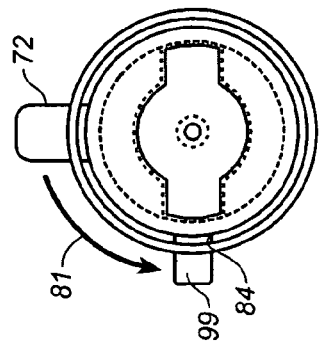
Figure 12C:
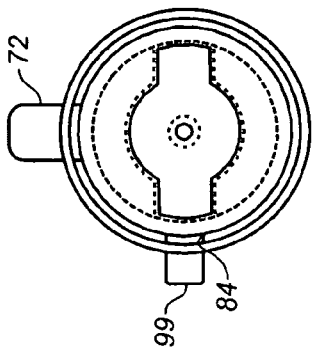
Figure 11A:
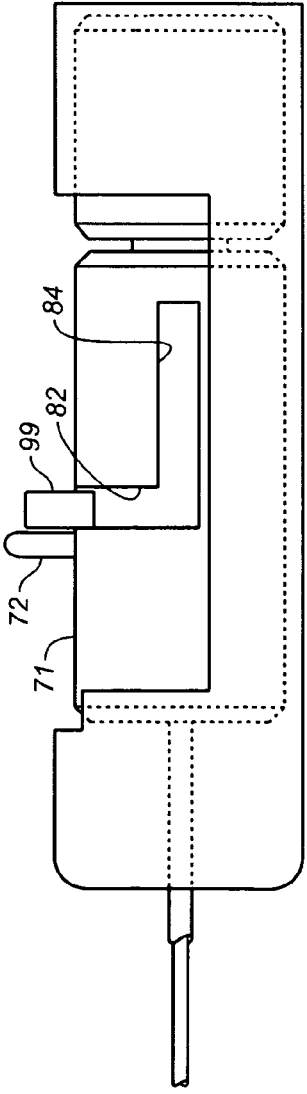
Figure 11B:
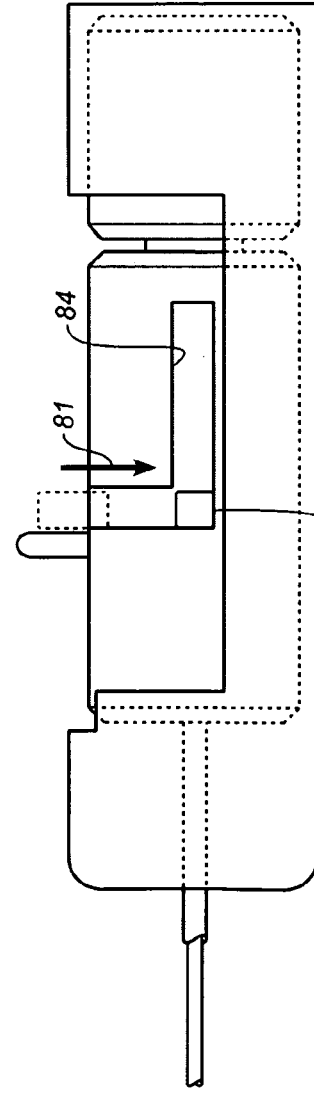
Figure 11C:
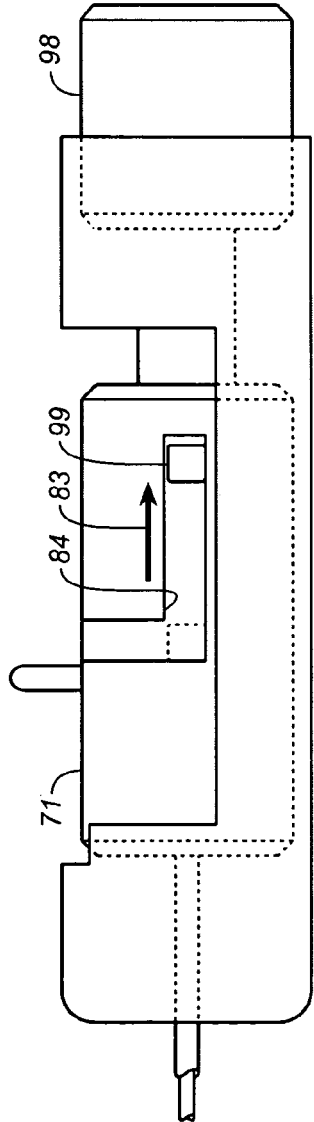

The release members (wires) 96d, e, f, can be retracted to release alternate more or less than all of the crowns of the stent or stent graft to be deployed, e.g., 52b, while tension on the steering members holding distal tip of the catheters centered in the vessel is maintained. When partial deployment of the stent graft is to take place, for example, three of the six crowns of the proximal stent are to be released before releasing all of the crowns, while As can be seen in FIG. 7B crowns 52b,d,f, have been released by movement of the release members 96d,e,f which do not have a corresponding steering member associated with it. As can be seen in FIGS. 8B and 7B the crown 52e and alternating crowns around the circumference of the proximal spring 60 remain captured. When the physician is ready to deploy the not yet deployed crowns, e.g., 52e, as is shown in FIG. 8C, release members 96c and 96a must first be retracted to unlock the tip locking mechanism of the steering members 88c and 88a, respectively. Once the expandable locking element (collet) 86c, 86a is released from interfering with the expanded portion of the steering member receiving opening 92c (shown), 92a (not shown), in FIG. 8. The steering members 88c, 88a can be retracted easily in the same manner as release member 96d,e,f were retracted, as described above, hereby releasing crown 52e of the proximal springs 60. A full release of the six crowns and the proximal spring 60 is shown in FIG. 7C which correlates to the condition observable in FIG. 8D. The expandable locking elements (collet) 86a,b,c, can be constructed by over molding polymer material on the PEEK tubing of the steering member tubular material. A cross wise straight cut (slot) through the center allows the two halves of the expanded portion to move towards each other, i.e., collapse, to allow them to pass through the narrow passage of the steering member receiving openings 92a,b,c. The release members 96a,b,c,d,e,f, are constructed of a tube or wire preferable made of stainless steel. The release member exhibits a low coefficient of friction interaction with the inside of the PEEK steering member tube. The distal anchor 62 could be made of a metallic material or could also be made of a polymer or hard plastic material as is well known in the art.

While the tip capture mechanism as described above describes the release member receiving openings, e.g., 92a, b,c, as being located in the distal anchor 62 the tip capture mechanism could be constructed so that the through holes in the splines (e.g., 90a,b,c) into which the steering members pass are configured to have an enlarged cavity (e.g., inverted cone shaped) to receive and lock the steering members. In such an embodiment the release members would extend beyond the splines to still capture the crowns of the proximal stent graft but such a capture arrangement would be in a distal capture space beyond the splines which are acting in this embodiment as the distal anchor. In this embodiment the capture space could be described as having a proximal tip capture space.

While the use of splines with through holes have been described above, an alternate arrangement for using a spline like arrangement could include using a catheter shaft with side hooks which guide the steering members and release members to the distal anchor. It might also be used to allow greater flexibly of manufacturing and design.

While the use of a collet-like tube expandable member has been described with respect to the distal anchor in the embodiments above, any similar configuration of side by side tubes or wires with one having an enlarged and locking portion to create a releasable mechanical interference in a distal anchor member could be used, as is known in the art. The only criteria would be that the configuration of the release member needed to unlock the steering member would generally have to be of a uniform diameter or cross section so that it can be pulled out easily and smoothly and not be subject catching on any corners, as might be the case if tube wire or tube like elements were used side by side where both had expandable portions which could interact to prevent their release.

Figure 13B:
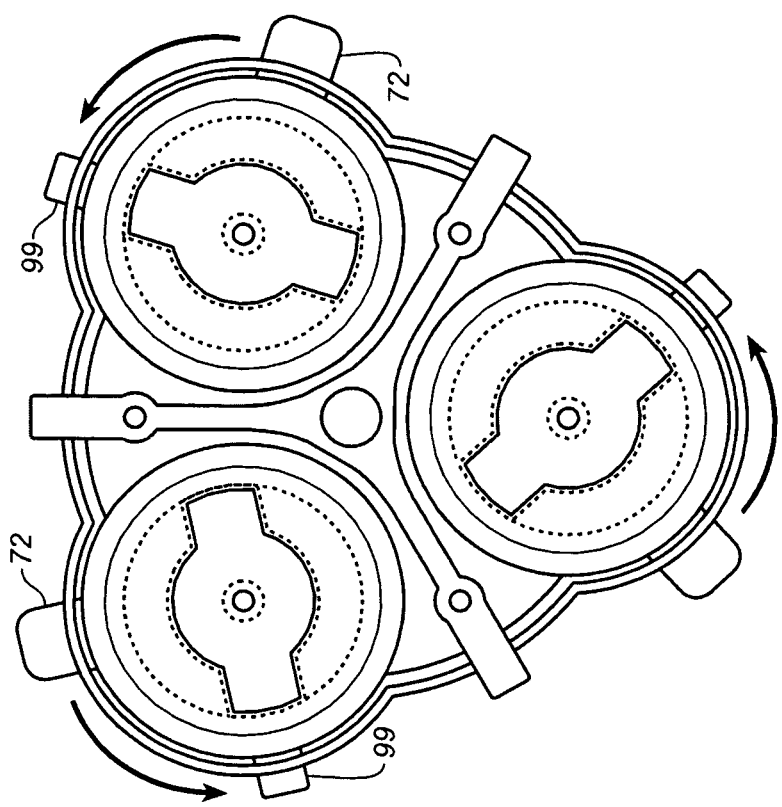
FIGS. 13A and 13B show end views of an embodiment of a handle housing arrangement for the delivery of the stent graft through a using a delivery catheter as shown in FIGS. 2A-E.
Figure 13A:
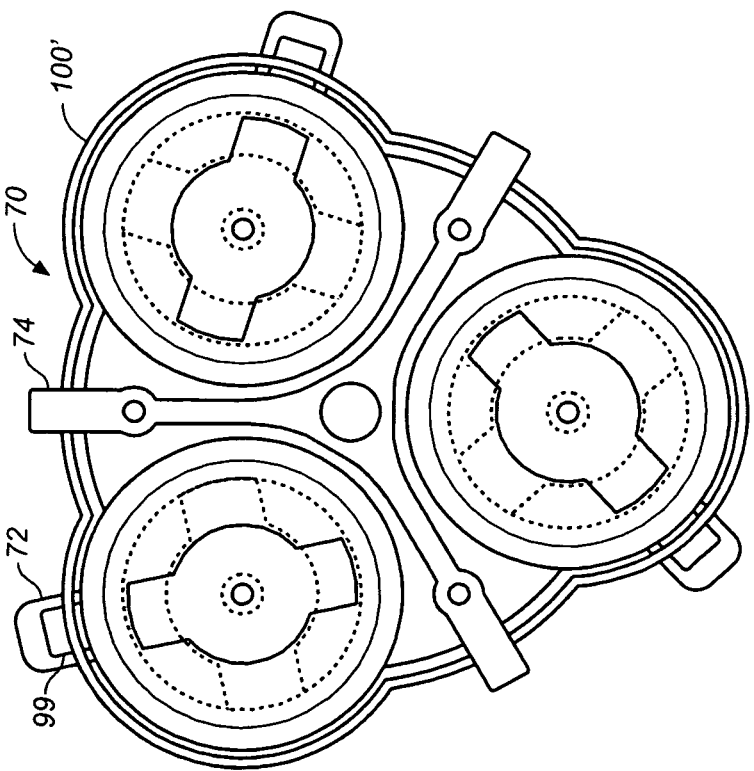
Figure 14:
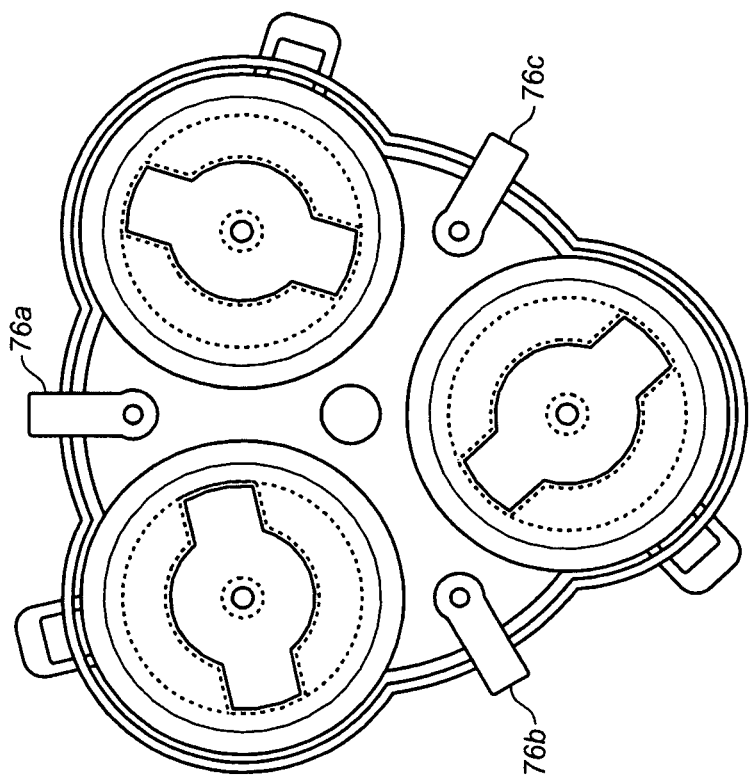
FIG. 14 shows alternate embodiment of end view an alternative embodiment of a handle housing for delivery of the stent graft using a delivery catheter as shown in FIGS. 2A-E.

The manipulation of the numerous steering and release members requires the individual or coordinated movement of the various wires and tubes in a handle. The handle 70, earlier mentioned, is now described in detail. Since the initial partial release of the approximately half or less crowns of the proximal spring of the stent graft to be deployed is a simple pull motion from the distal end of the catheter towards the proximal or handle end. The mechanism for pulling is a simple linear pulling motion and the three pull wires, i.e., release members 96*d,e,f*, can be connected to a single pull plate 74 or individual release member pull tabs 76*a,b,c*. Such plates and tabs are shown in FIGS. 13A, 13B, and 14.

Since steering of the catheter requires tension being applied to each of the steering members individually, it is necessary that each steering member have it's own point for application of force to influence movement of the end of the catheter as desired by the physician. During the time the steering member is under tension the release member contained within (at the core of) the steering member, in the present embodiment, must maintain its locked (forward) position so that the catheter steering using the locked end steering wire can take place. FIG. 9A shows the steering member and release member handle elements connected to the steering member and release member. A steering member, e.g., 88*a, b, c*, is fixed to a steering member control cylinder 71 and steering tab 72. Contained and configured to coaxially nest or coaxially slide within and with respect to the steering member control cylinder 71, a release member control element 98 with a control tab 99 is coaxially arranged with the steering member control cylinder 71.

The nested and coaxially arrangement of the two pieces is shown in FIG. 9B. The control tab 99 is shown positioned adjacent to and behind steering tab 72 so that an instances where both steering member and release member needs to move simultaneously and in a coordinated motion, they do so.

A handle housing 100 shown in FIGS. 10A, 10B, 11A, 11B, and 11C provides a housing for holding and connection to the common handle 70 at the proximal end of the delivery catheter (system) 40.

The operation of the steering member with respect to the steering tabs and control tabs will be described by referring to the side views and end views as shown in FIGS. 10A-12C. When the physician wishes to cause the steering or sideways movement of the end of the delivery catheter 40 it is necessary to create tension in the steering member which is accomplished by pressing proximally on both the steering tab 72 and control tab 99 and moving them proximately as shown in FIG. 10B by the arrow 78, and FIGS. 11A, and 12A. When a physician prepares to release or unlock the locked steering members, needed to retract the release member associated with each steering member, the release member control element 98 is allowed to rotate by applying force to the control tab 99 with respect to the steering member control cylinder 71 in circumferential slot 82. When the release member control element 98 by using the control tab 99 is rotated to the location of the unlocking slot (longitudinal) as shown by the arrow 81 in FIGS. 11B and 12B then the control tab of the release member control element 98 can be retracted along the unlocking slot 84 using a force applied to the end of control tab 99 in the direction shown by arrow 83 in FIG. 11C. Once the control tab 99 has reached the distal end of the unlocking slot 84, further movement of the control tab 99 will engage the end of the slot and also cause simultaneous proximal motion of the steering member control cylinder 71 in a proximal direction. The proximal movement of the steering member control cylinder 71 will cause release of the crowns of the proximal spring 60 as described above.

The embodiment described above three steering members (e.g., 92*a, b, c*) and six release members (e.g., 96*a,b,c,d,e,f*) are discussed and described. It is symmetrically convenient to have six release members evenly distributed around the circumference and three steering members similarly equally distributed, however, in instances where odd numbers of stent crowns are used it would be important to maintain the steering capability of the catheter so that in an configuration where five crowns are used on the proximal spring, there would be three steering members to provide three tensioning members to the steering function of the steerable delivery catheter while two crowns would be available for early or partial release. A person skilled in the art would decide how many steering and release members would most efficiently serve their purpose. In some steerable catheters it is convenient to rotate the catheter and only use one steering member, but in large diameter catheters, rotation of the catheters can be difficult because potential frictional resistance with the surrounding vascular wall structure and therefore is not recommended. So in the normal stent grafts where large French size catheters (>18 Fr) are being used it would be expected that it minimum of three steering members would be used.

FIGS. 13A and 13B show a configuration with three steering member control cylinders and their associated handle housing 100', where their respective steering tabs 72 and control tabs 99 are shown in an end view. This a configuration shows a single three arm (yoke) plate 74 that acts as a pull plate to simultaneously pull/retract the three release members which do not contribute to locking or unlocking of the steering members.

In another configuration as shown in FIG. 14, the three release members which do not contribute to locking or unlocking of the steering members can be individually manipulated by pull tabs 76*a*, 76*b*, 76*c*. The handle housing (e.g., 100 (100')) are connected the catheter shaft 80 so that axial tensile and compressive forces can be transmitted along the shaft and opposed by the steering members as they steering members are tensioned and released to bend the catheter shaft as can be seen in, for example in FIG. 3A and FIG. 3B.

A method of delivery a stent graft in accordance with the above described embodiments includes positioning a catheter at a treatment location, manipulating the catheter laterally at the treatment location to improve the chance of symmetric deployment, deploying approximately half the crowns of a proximal spring equally distributed around the perimeter at the proximal end of a stent graft, and further deploying previously undeployed crowns of the spring at the proximal end of the stent graft. Wherein the step of manipulating may involve manipulation of a releasable steering member. Wherein the step of deploying a approximately half the crown may involve moving the release members from a crown captured position to a crown released position. Wherein the step of deploying previously undeployed crowns may involve moving steering member release wires from a locked position to a release position and moving the steering member from a crown captured position to a crown released position. Wherein the step of manipulating may involve manipulation of one of at least two or more releasable steering members, one at least three releasable steering members or one of at least four releasable steering members.

It will be apparent to persons skilled in the relevant art that various changes in form and detail can be made therein without departing from the spirit and scope of the embodiments described. It will also be understood that each feature of each embodiment discussed herein, and of each reference cited herein, can be used in combination with the features of any other embodiment. Patents and publications discussed herein are incorporated by reference herein in their entirety.

What is claimed is:
1. A prosthesis delivery catheter comprising:
  a catheter shaft having a proximal end and a distal end, said distal end having a distal anchor;
  a steering member receiving opening disposed in said distal anchor;

a steering member extending along said catheter shaft from said distal anchor to a handle at said proximal end of said catheter shaft;

a release member extending along said catheter shaft from said distal anchor to a handle at said proximal end of said catheter shaft;

wherein said release member in a lock position has a distal end disposed to prevent a distal end of the steering member disposed in said steering member receiving opening from separating from said steering member receiving opening in said distal anchor, wherein when said release member is moved to a release position said distal end of said steering member is not prevented from separating from said steering member receiving opening in said distal anchor, and wherein when the steering member is disposed in said steering member receiving opening in the locked lock position, the steering member is configured to be placed in tension by steering tabs disposed in the handle such that tension applied to the steering tabs causes tension in the steering member to shorten a length of the catheter on the side of the steering member causing the catheter to bend.

2. The prosthesis delivery catheter of claim 1, wherein said steering member and said release member extend through a spline capturing an endoluminal prosthesis element in a proximal capture space defined by: said catheter shaft, said distal anchor, said spline, and at least one of said steering member and said release member.

3. The prosthesis delivery catheter of claim 2, wherein said spline has a through hole therein through which at least one of said steering member and said release member are configured to pass.

4. The prosthesis delivery catheter of claim 2, wherein said endoluminal prosthesis element has a proximal spring element.

5. The prosthesis delivery catheter of claim 4, wherein said endoluminal prosthesis element is part of a stent.

6. The prosthesis delivery catheter of claim 4, wherein said endoluminal prosthesis element is part of a stent graft.

7. The prosthesis delivery catheter of claim 2, wherein said steering member is a tube.

8. The prosthesis delivery catheter of claim 7, wherein steering member tube has an expandable locking element at a distal end thereof.

9. The prosthesis delivery catheter of claim 8, wherein said release member is a wire or a tube.

10. The prosthesis delivery catheter of claim 9 wherein in said lock position said release member is positioned within said expandable locking element of said steering member tube and said expandable locking element is disposed within said steering member receiving opening, and in said release position said release member is not positioned within said expandable locking element of said steering member tube.

11. The prosthesis delivery catheter of claim 9, wherein said wire or tube has an enlarged end locking portion.

12. The prosthesis delivery catheter of claim 2, wherein said steering member is a wire.

13. The prosthesis delivery catheter of claim 12, wherein the wire has an enlarged end portion.

14. The prosthesis delivery catheter of claim 13, wherein said release member is a wire.

15. The prosthesis delivery catheter of claim 14, wherein said wire that is the release member has an enlarged end locking portion.

16. The prosthesis delivery catheter of claim 1, further comprising:

at least one side hook extending from the catheter shaft to guide said steering member to the distal anchor, wherein a proximal capture space defined by said distal anchor, said catheter, said side hook, and at least one of said steering member and said release member captures an endoluminal prosthesis element.

17. The prosthesis delivery catheter of claim 1, wherein the release member extends beyond the distal anchor to act as barrier capturing an endoluminal prosthesis element in a distal capture space between said catheter shaft extending beyond said distal anchor and said release member.

18. The prosthesis delivery catheter of claim 17, where the distal anchor is configured as a rib in which said steering member is anchored and around which a portion of said endoluminal prosthesis element extending from said distal capture space can be positioned.

19. The prosthesis delivery catheter of claim 18, wherein said endoluminal prosthesis element has a proximal spring element.

20. The prosthesis delivery catheter of claim 18, wherein said steering member is a tube;

wherein steering member tube has an expandable locking element at a distal end thereof;

wherein said release member is a wire or a tube;

wherein in said lock position said release member is positioned within said expandable locking element of said steering member tube and said expandable locking element is disposed within said steering member receiving opening, and in said release position said release member is not positioned within said expandable locking element of said steering member tube.

21. A prosthesis delivery catheter comprising:

a catheter shaft having a proximal end and a distal end, said distal end having a distal anchor;

a plurality of proximally facing openings in said distal anchor;

a plurality of release members extending along said catheter shaft from said distal anchor to a handle at said proximal end of said catheter shaft;

a plurality of guide members disposed around the catheter shaft;

wherein in a delivery configuration a distal end of each release member is disposed in a respective opening and extends through a respective one of said guide members to define a proximal capture space defined by said distal anchor, said catheter shaft, said guide member, and said release member, wherein in the delivery configuration a crown of a plurality of crowns of a proximal spring stent of a prosthesis is captured in each proximal capture space, wherein at least one of the release members is controlled separately such that the at least one release member may be retracted to a release position wherein the release member does not define a portion of the respective proximal capture spaced such that the crown is released from the proximal capture space while at least one of the other release members remains in the delivery configuration capturing a respective crown in the respective proximal capture space.

22. The prosthesis delivery catheter of claim 21, wherein in a partially deployed configuration a plurality of the release members are in the release position such that the respective crowns are released from the respective proximal capture spaces and a plurality of the release members are in the delivery configuration such that the respective crowns are captured in the respective proximal capture spaces.

23. The prosthesis delivery catheter of claim 22, wherein in a deployed configuration all of the release members are in the release position such that the respective crowns are released from the respective proximal capture spaces.

24. The prosthesis delivery catheter of claim 23, further comprising:
- at least one steering member extending along said catheter shaft from said distal anchor to a handle at said proximal end of said catheter shaft, wherein in the delivery configuration a distal end of the steering member is disposed in a respective opening of the distal anchor and one of the release members is disposed within the steering member to lock said steering member in said opening, wherein the steering member in the delivery configuration is configured to be placed in tension by a steering tab disposed in the handle such that tension applied to the steering tab causes tension in the steering member to shorten a length of the catheter on the side of the steering member causing the catheter to bend.

25. The prosthesis delivery catheter of claim 24, wherein in the deployed configuration said steering member is also retracted such that the respective crown is released from the respective proximal capture space.

* * * * *